(12) United States Patent
Kerber

(10) Patent No.: US 10,195,459 B2
(45) Date of Patent: Feb. 5, 2019

(54) DEVICE FOR PHOTODYNAMICAL THERAPY OF CANCER

(71) Applicant: Tom Kerber, Stoney Creek (CA)

(72) Inventor: Tom Kerber, Stoney Creek (CA)

( * ) Notice: Subject to any disclaimer, the term of this patent is extended or adjusted under 35 U.S.C. 154(b) by 655 days.

(21) Appl. No.: 14/482,432

(22) Filed: Sep. 10, 2014

(65) Prior Publication Data

US 2015/0018751 A1    Jan. 15, 2015

Related U.S. Application Data

(63) Continuation-in-part of application No. 13/121,552, filed as application No. PCT/IL2009/000929 on Sep. 29, 2009, now abandoned.

(60) Provisional application No. 61/100,767, filed on Sep. 29, 2008.

(51) Int. Cl.
*A61N 5/06* (2006.01)
*A61K 41/00* (2006.01)
*A61N 5/00* (2006.01)

(52) U.S. Cl.
CPC .......... *A61N 5/062* (2013.01); *A61K 41/0061* (2013.01); *A61N 2005/007* (2013.01); *A61N 2005/0645* (2013.01); *A61N 2005/0652* (2013.01)

(58) Field of Classification Search
CPC .............................. A61N 5/062; A61K 41/0061
USPC .......................................................... 607/88
See application file for complete search history.

(56) References Cited

U.S. PATENT DOCUMENTS

| | | | |
|---|---|---|---|
| 6,290,713 B1 * | 9/2001 | Russell | A61N 5/0616 607/88 |
| 6,899,723 B2 | 5/2005 | Chen | |
| 7,503,927 B1 * | 3/2009 | Vetanze | A61N 1/0408 607/115 |
| 7,513,906 B2 * | 4/2009 | Passy | A61N 5/0613 607/88 |
| 2001/0051743 A1 * | 12/2001 | Gierskcky | A61K 31/22 560/155 |
| 2002/0183301 A1 * | 12/2002 | Rychnovsky | A61K 41/0076 514/185 |
| 2003/0216795 A1 * | 11/2003 | Harth | A61K 41/0071 607/88 |
| 2005/0099824 A1 * | 5/2005 | Dowling | A61B 1/0653 362/572 |
| 2005/0158687 A1 | 7/2005 | Dahm | |

(Continued)

FOREIGN PATENT DOCUMENTS

WO    WO 2010070277 A1 *    6/2010    .......... A61N 5/0616

OTHER PUBLICATIONS

International Search Report and Written Opinion dated Mar. 24, 2010 in related International Application No. PCT/IL2009/000929.

*Primary Examiner* — Gary Jackson
*Assistant Examiner* — Sebastian X Lukjan

(57) ABSTRACT

A method and device for photodynamic therapy for treating cancer. The method includes: providing a photodynamic therapeutic device for treating cancer. The provided device includes a plurality of light emitting diodes that are positionable in proximity of a patient's body and are adapted to provide a light fluence to a lesion area. The method also includes administering an effective dose of a photosensitizer in the lesion area; positioning the device in proximity to the patient's body; and irradiating the patient's body.

18 Claims, 12 Drawing Sheets

(56) References Cited

U.S. PATENT DOCUMENTS

| | | | |
|---|---|---|---|
| 2006/0020309 A1* | 1/2006 | Altshuler | A61B 18/203 |
| | | | 607/88 |
| 2007/0010506 A1 | 1/2007 | Chang et al. | |
| 2007/0168000 A1* | 7/2007 | Happawana | A61N 5/0601 |
| | | | 607/88 |
| 2007/0233208 A1* | 10/2007 | Kurtz | A61N 5/0613 |
| | | | 607/88 |
| 2007/0260296 A1 | 11/2007 | Porter et al. | |
| 2007/0299431 A1 | 12/2007 | Jakubowski et al. | |
| 2008/0031924 A1 | 2/2008 | Gilson et al. | |
| 2009/0040523 A1* | 2/2009 | Brukilacchio | A61B 1/0653 |
| | | | 356/432 |
| 2012/0116485 A1* | 5/2012 | Burgmann | A61B 5/0059 |
| | | | 607/90 |

* cited by examiner

DEVICE FOR PHOTODYNAMICAL THERAPY OF CANCER

CROSS-REFERENCE TO RELATED APPLICATIONS

This application is a Continuation-In-Part of U.S. patent application Ser. No. 13/121,552 filed on Mar. 29, 2011, now pending, which is the U.S. national phase entry of PCT Application No. PCT/IL2009/000929 filed on Sep. 29, 2009, now expired, which claims the benefit of U.S. Provisional Application No. 61/100,767 filed on Sep. 29, 2008. Each of these applications is hereby incorporated by reference in its entirety.

FIELD OF THE INVENTION

The present invention relates to a device of photodynamic therapy, and, more specifically, to a device adapted for photodynamic treating the embraceable body regions.

BACKGROUND OF THE INVENTION

Photodynamic therapy (PDT) is also called photoradiation therapy, phototherapy, or photochemotherapy. It was first used to treat cancer over 100 years ago. It is treatment that uses drugs, called photosensitizing agents, along with light to kill cancer cells. The drugs only work after they have been activated or "turned on" by certain kinds of light. Depending on the part of the body being treated, the photosensitizing agent is taken orally, injected into the bloodstream or put on the skin. After the drug is absorbed by the cancer cells, light is applied only to the area to be treated. The light causes the drug to react with oxygen, which forms a chemical that kills the cancer cells. PDT may also work by destroying the blood vessels that feed the cancer cells and by alerting the immune system to attack the cancer.

The period of time between when the drug is given and when the light is applied is called the drug-to-light interval. It can be anywhere from a couple of hours to a couple of days and depends on the drug used.

PDT can be used to treat some cancers, or conditions that may develop into a cancer if not treated (precancerous). It is used when the affected area or the cancer is on or near the lining of internal organs. This is usually with cancers or conditions that affect: the skin, the breast, the head, the neck, the mouth, the lung, the gullet (oesophagus), the stomach, the rectum and the bile ducts.

Breast cancer affects one in eight women during their lives. Breast cancer kills more women in the United States than any cancer except lung cancer. No one knows why some women get breast cancer, but there are a number of risk factors. Risks that you cannot change include (a) age; the chance of getting breast cancer rises as a woman gets older; (b) genes; there are two genes, BRCA1 and BRCA2 that greatly increase the risk; women who have family members with breast or ovarian cancer may wish to be tested; (c) personal factors; beginning periods before age 12 or going through menopause after age 55.

Other risks include being overweight, using hormone replacement therapy, taking birth control pills, drinking alcohol, not having children or having a first child after age 35 or having dense breasts.

Symptoms of breast cancer may include a lump in the breast, a change in size or shape of the breast or discharge from a nipple. Breast self-exam and mammography can help find breast cancer early when it is most treatable. Treatment may consist of radiation, lumpectomy, mastectomy, chemotherapy, and hormone therapy.

Breast cancer recurrences after mastectomy pose a therapeutic challenge with few surgical options. If disease is localized, surgical excision can be attempted. However, these lesions often are widespread throughout the chest wall or involve heavily irradiated tissue. Many patients have received aggressive chemotherapy with little to no local response and have exhausted most avenues for local control. Multiple studies show that photodynamic therapy (PDT) provides good tumor kill for primary cutaneous malignancies and suggest its effectiveness in ablating dermal lymphatic recurrences of breast cancer. Food and Drug Administration (FDA) approved uses for PDT include lung and esophageal lesions, but treatment of bladder, head and neck, and other tumor sites with novel approaches has been reported. PDT exploits the accumulation of photosensitizers into the tumor, which then is locally excited with visible light. Selectivity of treatment comes from the excretion of drug from normal tissue over time, promoting a concentration gradient within the tumor plus the location of the activating light. Treatment depth varies with the wavelength of light that activates the sensitizer used. The singlet oxygen that is produced during the transfer of energy from light source to drug disrupts plasma, nuclear, and mitochondrial cell membranes, resulting in apoptosis. Local edema and perivascular stasis occur rapidly, within hours of treatment. Tumor necrosis can be evident within 2 to 24 hours. Photofrin (dihematoporphyrin ether; Axcan Scandipharm, Birmingham, Ala.) is the only FDA-approved photosensitizer available for the treatment of cancer. The light source used to activate Photofrin (630 nm) is topically delivered via lasers by using diffusing catheters and is focused on skin surfaces by using a microlens. This modality has been previously reported in a small number of breast cancer patients with chest wall recurrence, with good responses.

U.S. Pat. No. 6,899,723 ('723) discloses methods and compounds for PDT of a patient's target tissue, using a light source that preferably transmits light to a treatment site transcutaneously. The method provides for administering to the subject a therapeutically effective amount of a targeted substance, which is either a targeted photosensitizing agent, or a photosensitizing agent delivery system, or a targeted prodrug. This targeted substance preferably selectively binds to the target tissue. Light at a wavelength or waveband corresponding to that which is absorbed by the targeted substance is then administered. The light intensity is relatively low, but a high total fluence is employed to ensure the activation of the targeted photosensitizing agent or targeted prodrug product. Transcutaneous PDT is useful in the treatment of specifically selected target tissues, such as vascular endothelial tissue, the abnormal vascular walls of tumors, solid tumors of the head and neck, tumors of the gastrointestinal tract, tumors of the liver, tumors of the breast, tumors of the prostate, tumors of the lung, nonsolid tumors, malignant cells of the hematopoietic and lymphoid tissue and other lesions in the vascular system or bone marrow, and tissue or cells related to autoimmune and inflammatory disease.

In accordance with '723, method of therapeutically treating a target tissue provides destroying or impairing target cell by the specific and selective binding of a photosensitizer agent to the target tissue, cell, or biological component. At least a portion of the target tissue is irradiated with light at a wavelength or waveband within a characteristic absorption waveband of the photosensitizing agent. It is contemplated that an optimal total fluence for the light administered to a patient is determined clinically, using a light dose escalation trial. The total fluence administered externally during a treatment preferably is in the range from 500 Joules to 70,000 Joules.

It should be emphasized that according data published by the US National Cancer Institute, maximal penetration depth achievable for photodynamic therapy is about 1 cm. Practically, depth penetration available for reliable photodynamic therapy can be performed at the penetration depth of 2-3 mm. Providing a photodynamic therapy generating high-energy light fluence characterized by greater depth of radiation penetration into tissues of the patient's body is an unmet and long-felt need.

SUMMARY OF THE INVENTION

It is hence one object of the invention to disclose a method of photodynamic therapy for treating cancer. The aforesaid method comprises the steps of (a) providing a photodynamic therapeutic device for treating cancer; said device comprises a plurality of light emitting diodes positionable in proximity of a patient's body adapted to provide a light fluence to a lesion area and cooling means; (b) administering an effective dose of a photosensitizer in a lesion area of said patient's body; (c) positioning the device in proximity of said device to said patient's body; (d) irradiating said patient's body.

It is a core purpose of the invention to provide the step of irradiating said lesion area which is characterized by power density ranging between 1 mW/cm$^2$ and 10,000 mW/cm$^2$ and treatment duration ranging between 150 sec and 3600 sec such that density of total energy incident to said lesion area is in a range between 0.01 J/cm$^2$ and 100 J/cm$^2$, thereat said step of irradiating said patient's body is performed by said photodynamic therapeutic device having a luminous surface of an area which is greater than 10 cm$^2$.

A further object of the invention is to disclose the device positioned in proximity of said patient's body in a location selected from the group consisting of a breast, an arm, a leg, a neck, an abdomen and any combination thereof.

A further object of the invention is to disclose a mode of device operation is selected from the group consisting of a continuous mode, a pulse mode, an intermittent mode and any combination thereof.

A further object of the invention is to disclose the step of positioning the device in proximity of said patient's body further comprising a step of preliminary positioning a silicon spacer therebetween.

A further object of the invention is to disclose the step of irradiating at maximum light intensity at at least one wavelength selected from the group consisting of: a wavelength of about 630 nm performed in coordination with said preceding step of administering an effective dose of a photosensitizer 5-aminolaevulinic acid (5-ALA); a wavelength of about 585 to about 740 nm performed in coordination with said preceding step of administering an effective dose of a photosensitizer 5,10,15,20-tetrakis(m-hydroxyphenyl) chlorin (Foscan); a wavelength of about 570 to about 670 nm is performed in coordination with said preceding step of administering an effective dose of a photosensitizer methyl aminolevulinate (Metvix); a wavelength of about 615 to about 800 nm performed in coordination with said preceding step of administering an effective dose of a photosensitizer Pd-bacteriopheophorbide (Tookad); a wavelength of about 600 to about 750 nm performed in coordination with said preceding step of administering an effective dose of a photosensitizer concentrated distillate of hematoporphyrins (Photofrin); a wavelength of about 450 to about 600 nm performed in coordination with said preceding step of administering an effective dose of a photosensitizer verteporfin (Visudyne) and any combination thereof.

A further object of the invention is to disclose the step of irradiating performed by said plurality of emitting diodes distributed along an inner surface of an annular structure.

A further object of the invention is to disclose the step of irradiating performed by LEDs grouped in a plurality of cooled units comprising at least two diodes; said cooled units are distributed along said inner surface of said annular structure.

A further object of the invention is to disclose the step of positioning said device in proximity of said patient's breast further comprising a step of adjusting a length of said annular structure according to a patient's breast size.

A further object of the invention is to disclose the step of positioning said device in proximity of said patient's breast further comprising steps of disposing said patient on a bearing surface in a prone position and putting in said patient's breast in said annular structure so that said annular structure embraces thereof and/or positioning the device in proximity of said patient's breast is performed frontally.

A further object of the invention is to disclose the light intensity gradually increasing over treatment time, allowing each measure of depth to receive an effective amount of light until that depth is treated.

A further object of the invention is to disclose a device for photodynamic therapy for treating cancer. The aforesaid device comprises a plurality of light emitting diodes postionable in proximity of a patient's body adapted to provide a light fluence to a lesion area and cooling means.

It is a core purpose of the invention to provide the device having a luminous surface positioned in proximity of the patient's body part to be treated and having an area which is greater than 10 cm$^2$.

A further object of the invention is to disclose the device configured for irradiating said lesion area is characterized by power density ranging between 1 mW/cm$^2$ and 10,000 mW/cm$^2$ and treatment duration ranging between 150 sec and 3600 sec such that density of total energy incident to said lesion area is in a range between 0.01 J/cm$^2$ and 100 J/cm$^2$.

BRIEF DESCRIPTION OF THE DRAWINGS

In order to understand the invention and to see how it may be implemented in practice, a plurality of embodiments is adapted to now be described, by way of non-limiting example only, with reference to the accompanying drawings, in which.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, are adapted to remain apparent to those skilled in the art, since the generic principles of the present invention have been defined specifically to provide a photodynamic therapeutic device and a method of using thereof.

The term 'photodynamic therapy (PDT)' hereinafter refers to therapy that uses laser, or other light emitting diodes, combined with a light-sensitive drug (sometimes called a photosensitizing agent) to destroy cancer cells.

The term 'lesion area' hereinafter refers to an area of internal cancerated tissues to be treated. The power and energy density values in the present invention relate to the aforesaid lesion area.

LED arrays employed as a light source during photodynamic therapy (PDT) can extend the effective penetration for light delivery so that it may be applied to treatment of tumours at depths of more than one centimeter. Tumour range Enhancement that could be treated by PDT is beyond the current methods providing one centimeter PDT accessibility.

The hypothesis is that a powerful water cooled LED array that can achieve sufficient light levels through more than one centimeter of mammary tissue that activate photosensitizer effectively to cause tumour cell death in a syngeneic mouse model of breast cancer.

LEDs are a more recent light delivery system with wavelength specificity and high fluence rates. The cooling system enables the delivery of extremely high fluence rates without risk of thermal damage due to the heat output of the LED arrays. This system allows external exposure to extremely high light levels and takes advantage of scattering to deliver sufficient light to activate photosensitizer to tissue depths not accessible to current light delivery systems.

A photosensitizing agent is a drug that makes cells more sensitive to light. Once in the body, the drug is attracted to cancer cells. It does not do anything until it is exposed to a particular type of light. When the light is directed at the area of the cancer, the drug is activated and the cancer cells are destroyed. Some healthy, normal cells in the body will also be affected by PDT, although these cells will usually heal after the treatment.

About 5% to 19% of breast cancer patients suffer from chest wall recurrences after mastectomy, and these breast cancer recurrences have a high impact on physical and psychological well-being. Although surgery and radiation therapy are standard treatments for chest wall recurrences after mastectomy, PDT shows promise in treating these patients, according to the researchers.

Figure 1:
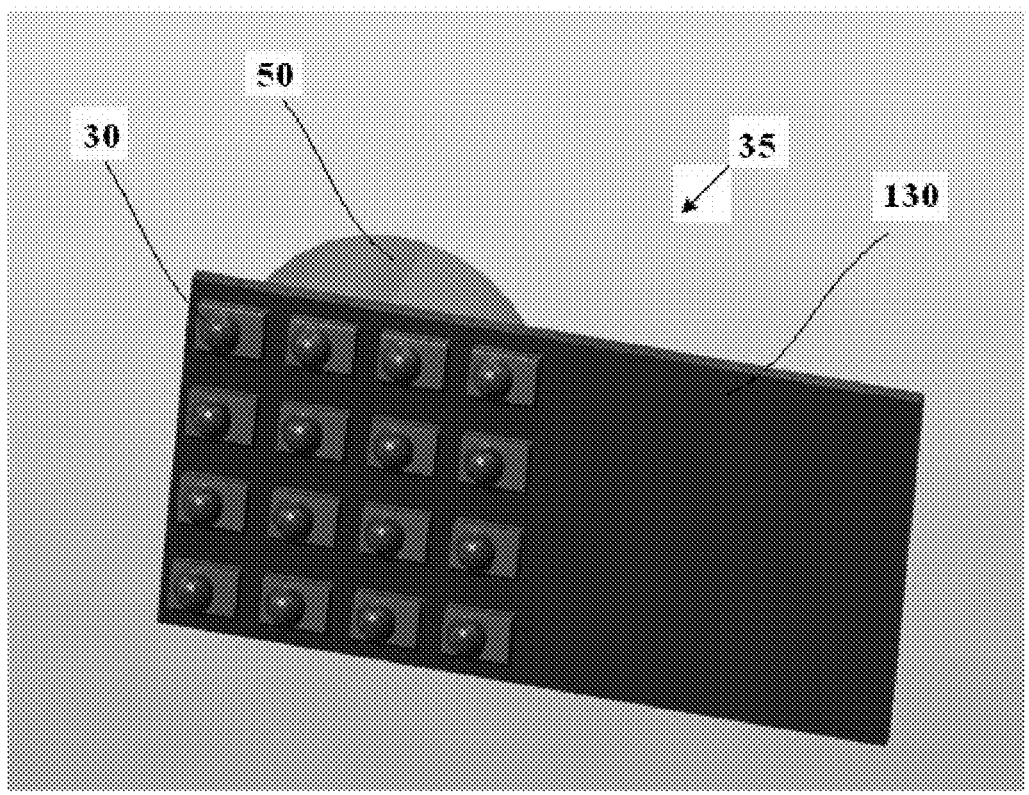
FIG. 1 is an isometric view of the LED unit.

Reference is now made to FIG. 1, presenting an LED unit 35 comprising a matrix of LEDs 30 disposed on a base plate 130. A passage 50 accommodating a coolant is attached to the back of the plate 130. Thus, the heat generated by the LEDs 30 is extracted by means of the coolant circulating in the cooling loop.

Figure 2:
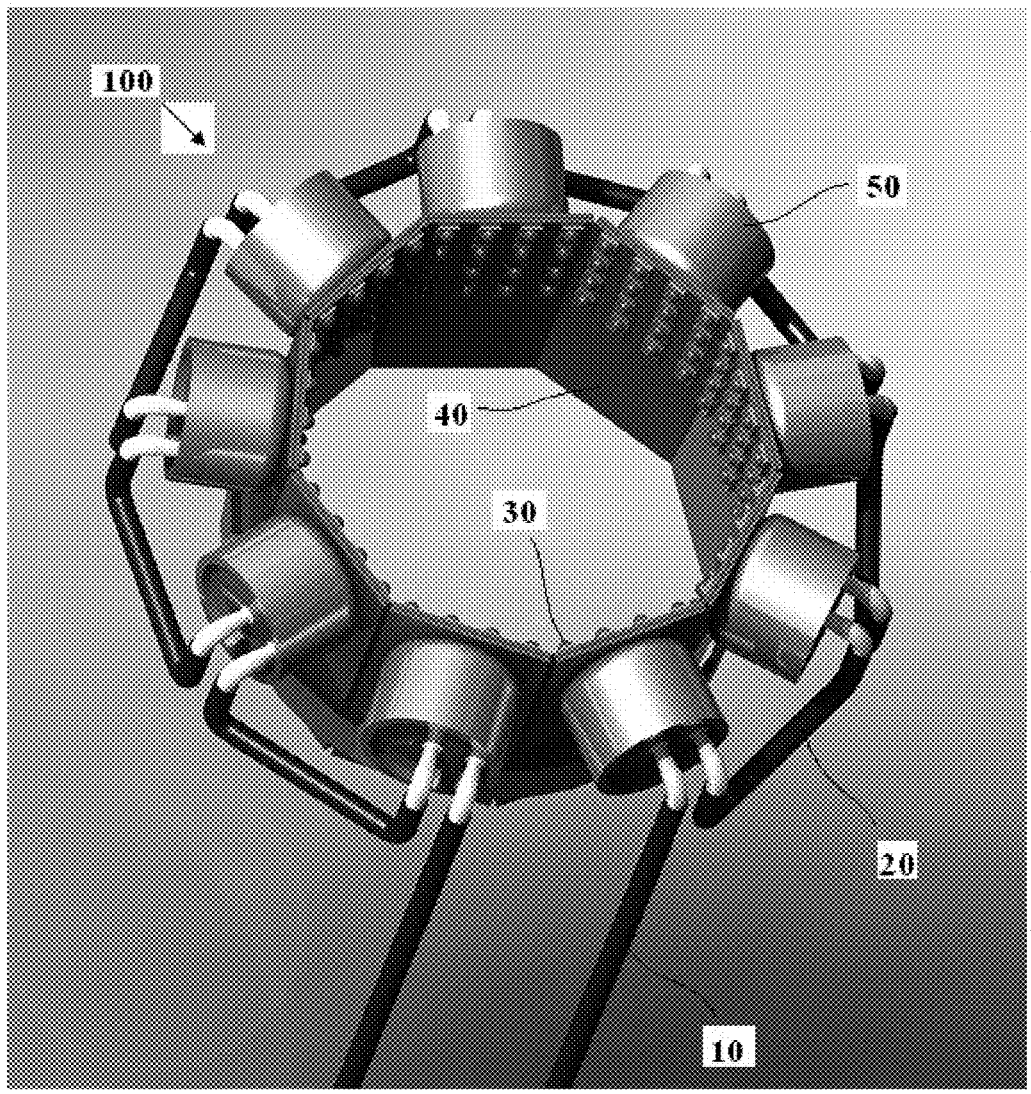
FIG. 2 is an isometric view of the photodynamic therapeutic device.

Reference is now made to FIG. 2, showing a PDT device 100 comprising an annular structure 40, LEDs 30 disposed at an inner surface of the aforesaid annual structure 40, the passages 50 accommodating the coolant circulating through feeding pipes 10 and 20. A strap 80 fixates the structure 40 on the patient's breast.

Figure 3:
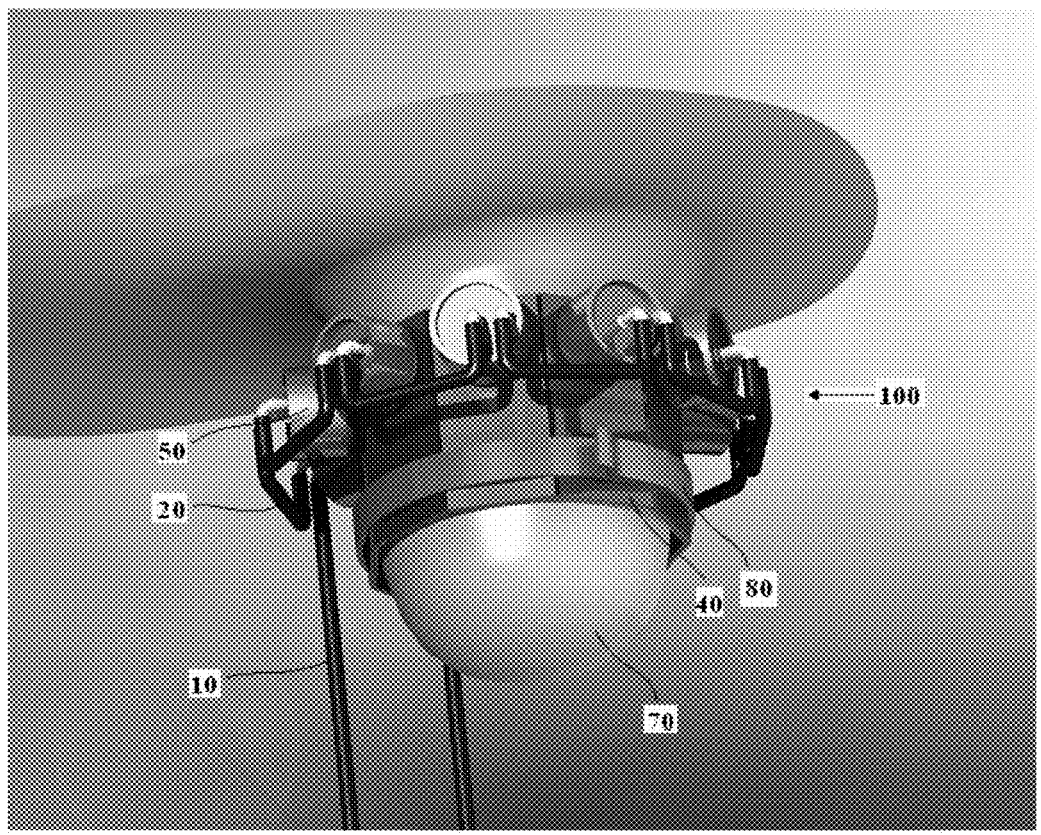
FIG. 3 is an isometric view of the photodynamic therapeutic device attached to the patient's breast.

Reference is now made to FIG. 3, presenting the device 100 attached to a patient's breast 70. The light emitted by the LEDs 30 (not shown) propagates into the patient's breast 70 and affects a sensitizer concentrated in the lesion area. PDT exploits the accumulation of photosensitizers into the tumor, which then is locally excited with visible light. Selectivity of treatment comes from the excretion of drug from normal tissue over time, promoting a concentration gradient within the tumor plus the location of the activating light. Treatment depth varies with the wavelength of light that activates the sensitizer used. The singlet oxygen that is produced during the transfer of energy from light emitting diode to drug disrupts plasma, nuclear, and mitochondrial cell membranes, resulting in apoptosis. Local edema and perivascular stasis occur rapidly, within hours of treatment.

The proposed device creates high light intensity in the lesion area to provide required light fluence in shorter period of time. The heat generated by the LED is extracted by the coolant circulating in the passages 50. The proposed arrangement allows safely attaching high intensity light emitting diode to the patient's body.

Figure 4:
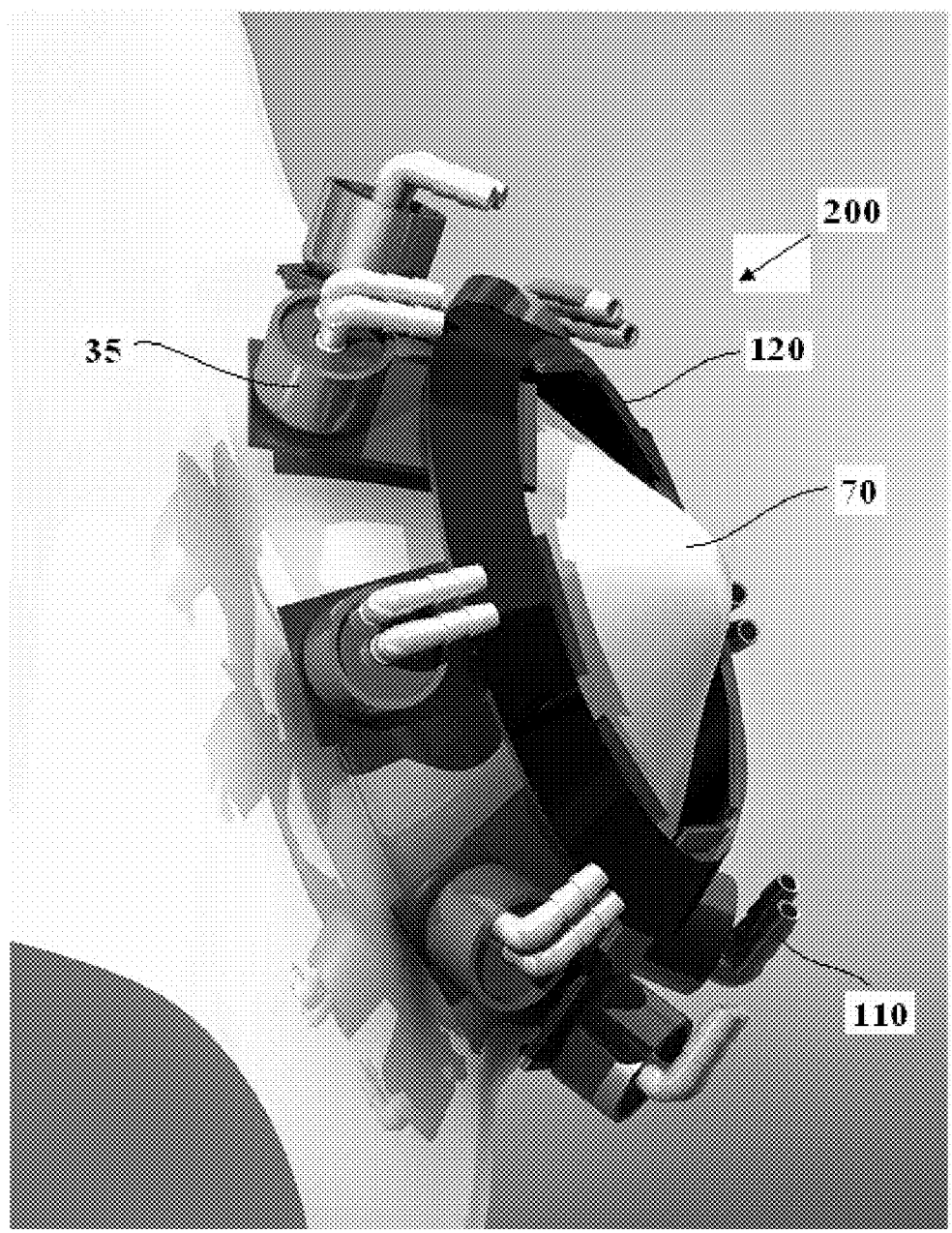
FIG. 4 is a side view of the alternative embodiment of the photodynamic therapeutic device attached to the patient's breast.
Figure 5:
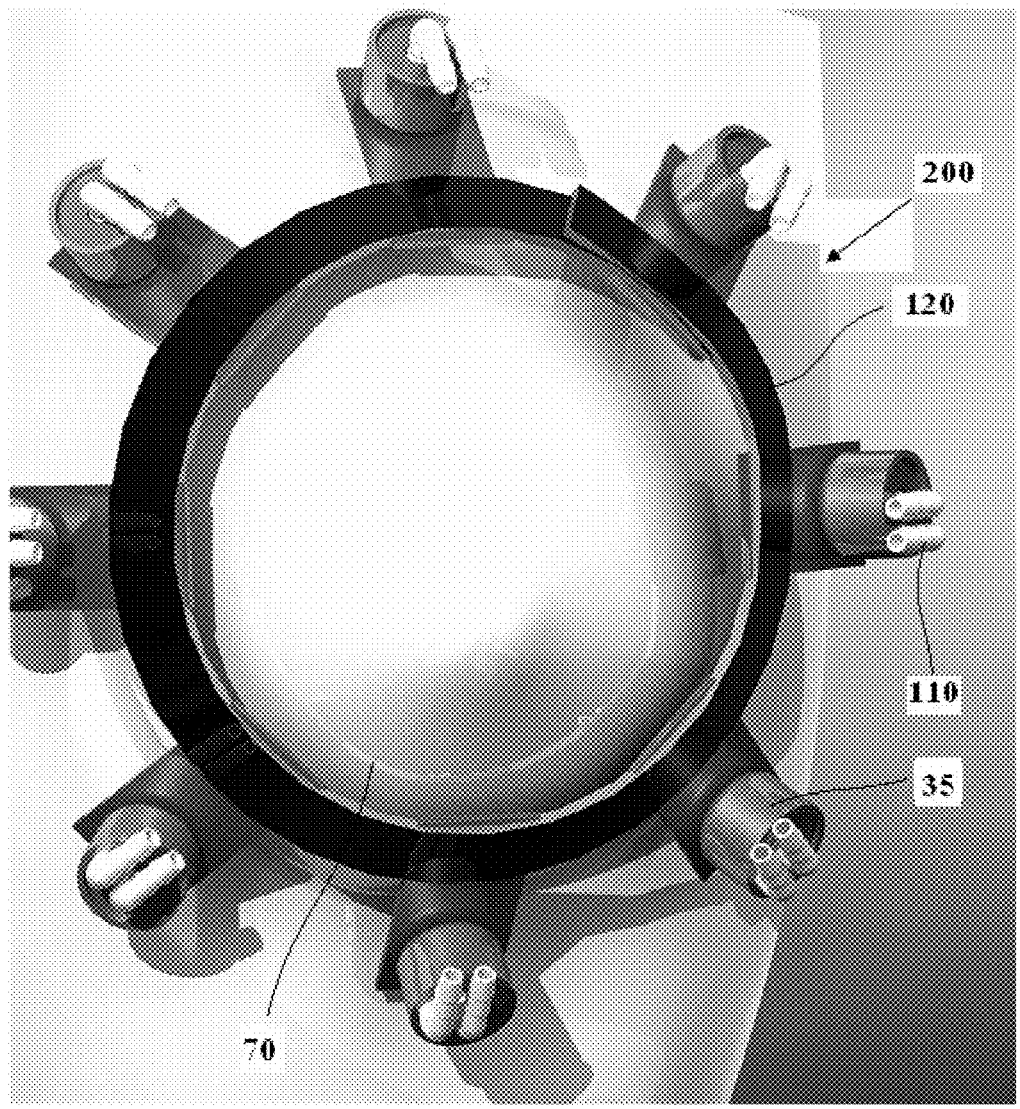
FIG. 5 is a front view of the alternative embodiment of the photodynamic therapeutic device attached to the patient's breast.

Reference is now made to FIGS. 4 and 5, shown side and front views of an alternative embodiment 200 of the PDT device, respectively. The configuration of the device 200 is conformed to a form of the patient's breast 70. The light units 35 are tilted relative to an annular structure 120. Adjustment of a length of the annular structure 120 according to a size of the patient's breast 70 is in a scope of the current invention.

Figure 6:
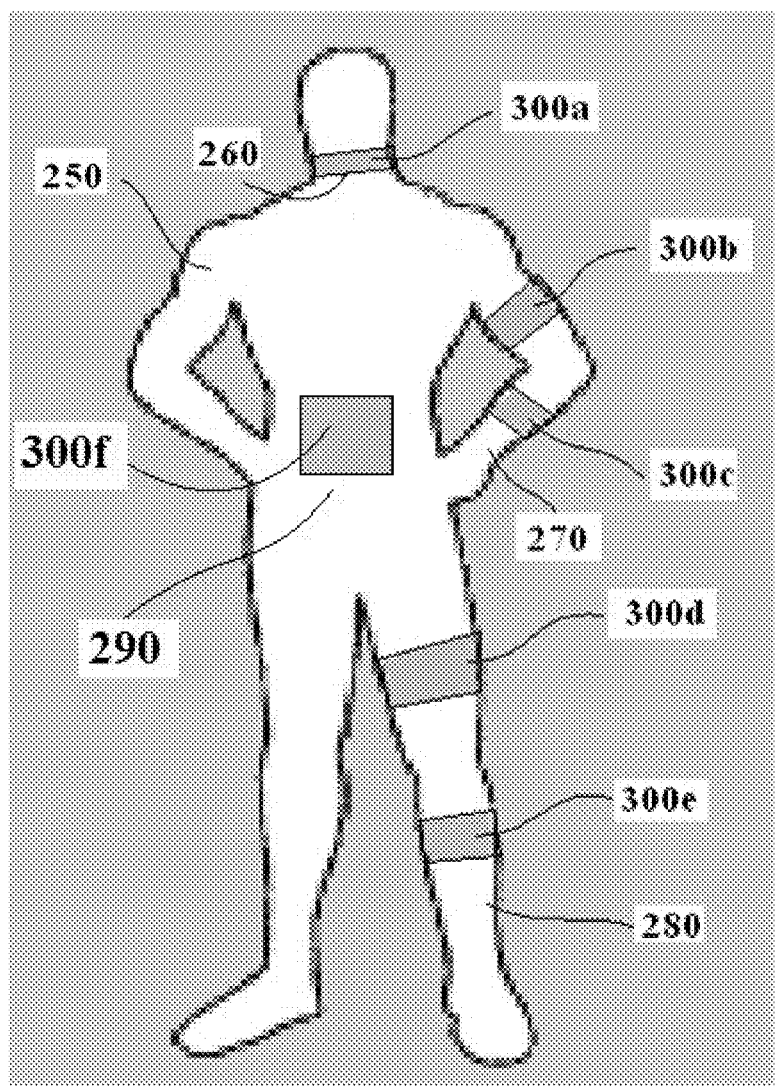
FIG. 6 is a schematic diagram of the photodynamic therapeutic device locations on the patient's body.

Reference is now made to FIG. 6, presenting optional body locations where the proposed therapeutic device can be attached. The therapeutic devices are attached to the patient's body 250 at a neck 260 (300a), an arm 270 (300b and 300c), a leg 280 (300d and 300e) and abdomen 290 (300f).

In accordance with one embodiment of the current invention, a photodynamic therapeutic device for treating cancer comprises at least one light emitting diode attachable to a patient's body adapted to provide an effective fluence to a lesion area. The aforesaid device further comprises an annular structure embracing the patient's body and a passage connectable to a cooling loop providing a circulative coolant into the passage. The light emitting diode is secured to an inner surface of the structure. The coolant accommodated in the passage is adapted for removing heat generated by the light emitting diodes. The annular embracing structure has 5 Rebel LEDs per cm. Each rebel yields 700 mw of light power. The aforesaid structure provides total of 3500 mw per $cm^2$. The LEDs have the means for internal cooling of the LEDs.

The used LED (Rebel by Phillips) is 100 times more powerful and has a thermal heat pad area common in the prior art while we keep the operating temperature under 50 degrees C.

Our research has shown that when a light emitting diode is wrapped around the breast that the light that is available at the center of the breast is a summation of the light that comes from each of the segments surrounding the breast.

90 degrees of light around a breast would yield ¼ of the fluence at the center of a breast to that which is 360 degrees (this results in 4× the light fluence) and probably adds an additional 1-2 cm of additional breast penetration depth. This is only important effect when the light fluence is high enough at the surface.

An example: 15 segments would be required to surround the breast due to the circumference of the breast (15") and the size of each segment (1").

The flexible "annular structure" comprises 5 to 15 small platforms or segments (hereafter referred to as segments) that are coupled together by a mechanical linkage of some type (fabric, Velcro, flexible material (silicone, ect. . . . )). Each one of the segments is small enough to cover some area say 2.5 cm×2.5 cm to say 4 cm×4 cm.

Each one of the segments is not flexible, because the very high heat removal that is required to keep the LEDs cool.

Each segment would contain 2 to 40 high power LEDs and would require up to 100 watts of heat removal for each segment.

Each segment would contain a 0.005" thick circuit board with direct LED soldered contact copper to a liquid heat removal chamber with turbulent liquid flow to remove the maximum heat from the segment.

Each one of the segments would have a clear silicone spacer mat 0.3-0.5 cm thick directly in front of the LEDs to protect and to remove the possibility of the lens of the LED directly coming into contact with the skin and causing direct heat transfer.

A tumor requires an extremely large fluence (10,000 mW/cm$^2$) at the surface of a breast to have enough light "effective fluence" (50 mW/cm$^2$) to activate the drug to treat the tumor at a distance 4 cm into the breast tissue. I think that until our patent these type of light levels described in various patents by many inventors have never been thought of for PDT.

According to preclinical investigations performed in mice, the most effective dosage resulting in full tissue recovery is characterized by the following parameters:

Power density ranging between 1 mWcm$^2$ and 10,000 mW/cm$^2$;

Treatment duration ranging between 150 sec and 3600 sec;

Total energy density which is incident to the lesion area is in a range between 0.01 J/cm$^2$ and 100 J/cm$^2$.

The interdependence between power density and treatment duration brings with it limitations in the treatment procedure: Cancer cells exposed to irradiation at a power density lower than 1 mW/cm$^2$ are responsive. At a power density greater than 10,000 mW/cm$^2$, tissues are likely to undergo burning due to thermal effects. In other words, the aforesaid values of total energy density incident on the cancer tissue should be within the range of the energy density limited by the sensibility threshold on the low density side and tissue burning on the high density side.

Results of preclinical trials are presented in Tables 1 and 2. Table 1 depicts a set of experiments on mice. The presented data characterize power densities and energy densities which are incident on the cancer tissue. Treatment durations are also reported. Table 2 provides medical results of the experiment. In the column of number of mice with response to treatment, the first number corresponds to mice with a more than 50% reduction of tumour size following the treatment*. The second number is a total number of samples exposed to a specific light dose.

TABLE 1

| Light dose | Joules delivered Joules/cm$^2$ | Time of treatment Seconds | Light Intensity at tumor surface mW/cm$^2$ |
|---|---|---|---|
| High dose light A | 35 | 300 | 114 |
| Low dose light B | 7 | 60 | 114 |
| Low dose light C | 5 | 600 | 8.3 |
| Low dose light D | 0.01 | 1200 | 0.83 |

TABLE 2

| Light dose | Tissue thickness** (cm) | Number of treatments | Number of mice with response to treatment* |
|---|---|---|---|
| High dose light A | 0 | 1 | 4/5 |
| Low dose light B | 0 | 3 | 8/10 |
| Low dose light C | 2 | 3 | 4/9 |
| Low dose light D | 4 | 3 | 2/10 |
| Control-No light | 0 | 0 | 0/10 |

**Tissue thickness refers to a thickness of pork tissue through which the cancer tumour in the mouse was irradiated. The dimension of the tumour was larger than 1 cm.

Figure 7:
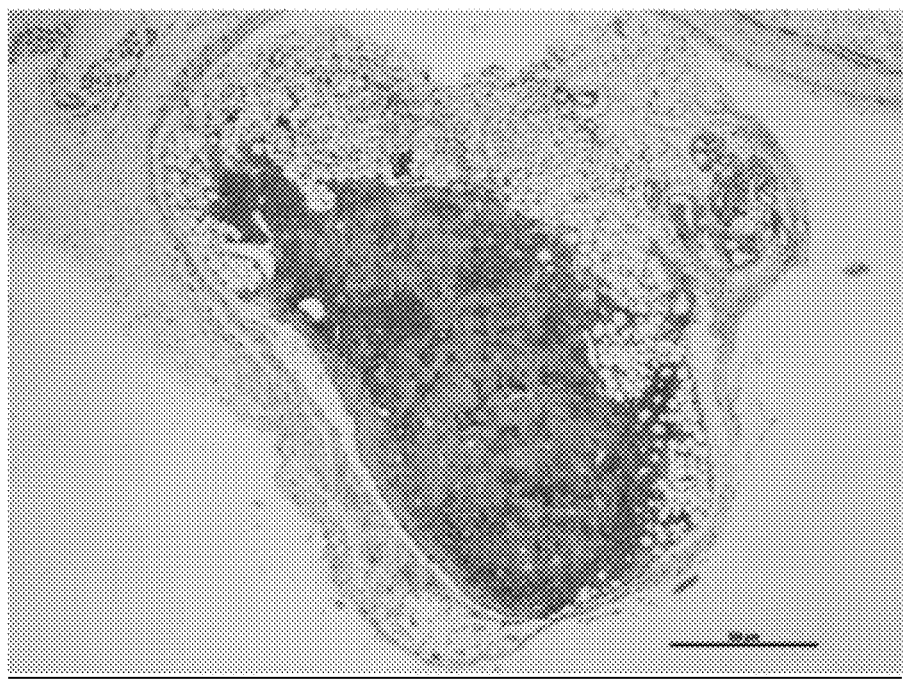
FIG. 7 is a photo of a remnant fibrous tissue following remission of a breast cancer tumour by photodynamic therapy.

Reference is now made to FIG. 7, presenting a remnant fibrous tissue following remission of a breast cancer tumour by photodynamic therapy using the light system of the present invention. There are no tumour cells visible. This figure is representative of the pathology to date in animals that have displayed remission in this experiment.

Figure 8:
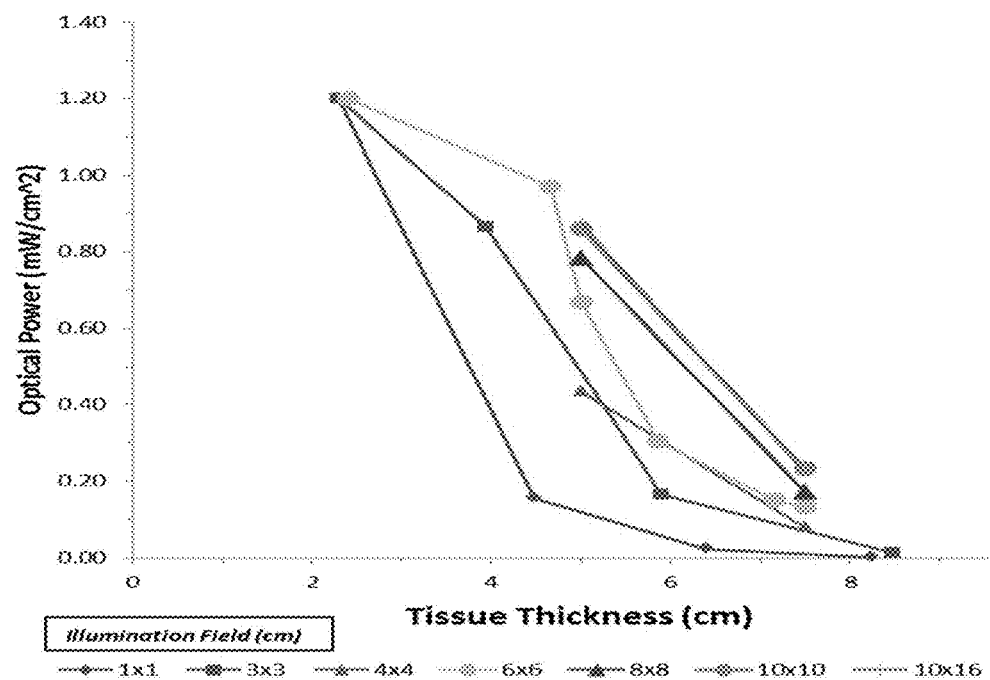
FIG. 8 is a graph of light intensity dependence on penetration depth within chicken breast.

Reference is now made to FIG. 8, presenting experimental data concerning intensity profile depending on a penetration depth. It is shown that the penetration depth increases with extension of luminance body. As it appears from FIG. 8, 1 cm$^2$ luminance body provides power density 0.2 mW/cm$^2$ at penetration depth of about 4 cm, while the same power density is obtained at the penetration depth of about 8 cm with a 100 cm$^2$ luminance body.

Figure 9:
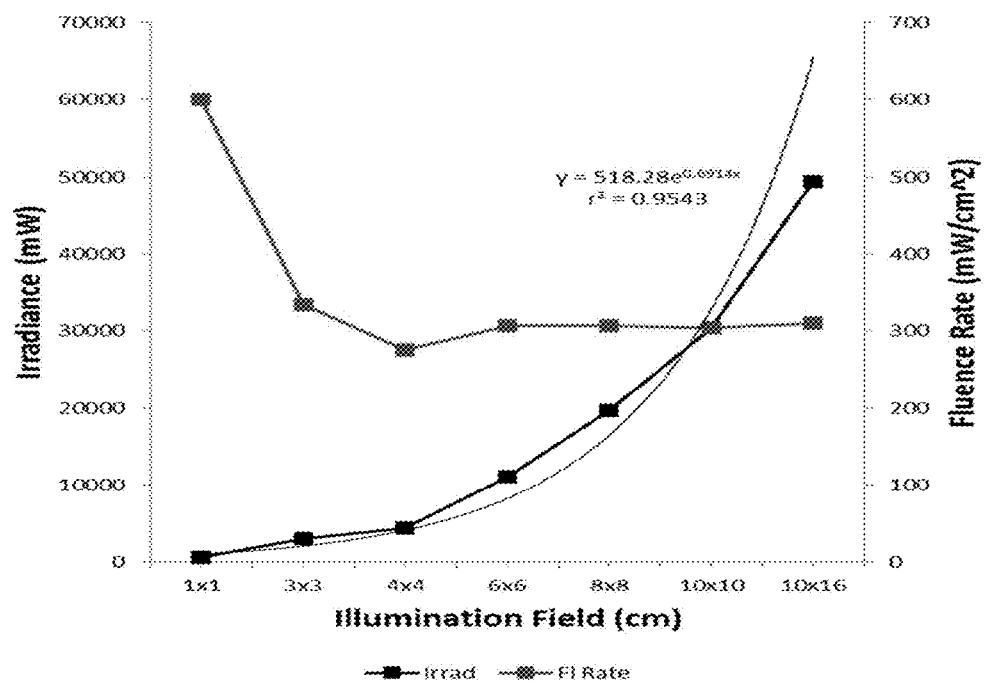
FIG. 9 shows graphs of irradiance and fluence rate depending on luminous area.

Reference is now made to FIG. 9, presenting graphs of irradiance and fluence rate depending on luminous area. The irradiance and fluence rate curves were measured at fixed penetration depth. Pursuant to graph comparison, a most effective LED arrangement has the luminous surface greater than about 10 cm$^2$.

In Table 3, the first row corresponds to the luminous area with LEDs that were used in chicken breast experiment while the rest of the rows provide model treatment protocol applicable to human.

TABLE 3

| 1.875 LEDs/cm2 3.75 W/cm2 | | | | LED power | Mouse Study LEDs Kilojoules delivered in | | | |
|---|---|---|---|---|---|---|---|---|
| cm (X) | cm (Y) | cm2 | Kilowatts | eff. @ 10% | 60 s | 3600 s (1 hr) | Applications | |
| 10 | 16 | 160 | 0.60 | 0.060 | 0.004 | 0.2 | Panel | |
| 35 | 10 | 350 | 1.31 | 0.131 | 0.008 | 0.5 | 14" × 4" | Arm |
| 50 | 10 | 500 | 1.88 | 0.188 | 0.011 | 0.7 | 20" × 4" | Thigh |

TABLE 3-continued

| 1.875 LEDs/cm2 3.75 W/cm2 | | | LED power | Mouse Study LEDs Kilojoules delivered in | | | |
|---|---|---|---|---|---|---|---|
| cm (X) | cm (Y) | cm2 | Kilowatts | eff. @ 10% | 60 s | 3600 s (1 hr) | Applications |
| 90 | 10 | 900 | 3.38 | 0.338 | 0.020 | 1.2 | 36" × 4" Waist |
| 90 | 15 | 1350 | 5.06 | 0.506 | 0.030 | 1.8 | 36" × 6" Waist |
| 110 | 15 | 1650 | 6.19 | 0.619 | 0.037 | 2.2 | 43" × 6" Waist/Chest |
| 130 | 15 | 1950 | 7.31 | 0.731 | 0.044 | 2.6 | 51" × 6" Waist/Chest |

Similar to the previous table 3, in table 4, the first row corresponds to a luminous area with more powerful LEDs then that were used in chicken breast experiment. It should be emphasized that, geometric configuration of the device for photodynamic therapy is adapted for a specific tumour location in the patient's body.

TABLE 4

| 1.875 LEDs/cm2 3.75 W/cm2 | | | LED power | Today's LEDs capability Kilojoules delivered in | | | |
|---|---|---|---|---|---|---|---|
| cm (X) | cm (Y) | cm2 | Kilowatts | eff. @ 25% | 60 s | 3600 s (1 hr) | Applications |
| 10 | 16 | 160 | 0.60 | 0.150 | 0.009 | 0.5 | Panel |
| 35 | 10 | 350 | 1.31 | 0.328 | 0.020 | 1.2 | 14" × 4" Arm |
| 50 | 10 | 500 | 1.88 | 0.469 | 0.028 | 1.7 | 20" × 4" Thigh |
| 90 | 10 | 900 | 3.38 | 0.844 | 0.051 | 3.0 | 36" × 4" Waist |
| 90 | 15 | 1350 | 5.06 | 1.266 | 0.076 | 4.6 | 36" × 6" Waist |
| 110 | 15 | 1650 | 6.19 | 1.547 | 0.093 | 5.6 | 43" × 6" Waist/Chest |
| 130 | 15 | 1950 | 7.31 | 1.828 | 0.110 | 6.6 | 51" × 6" Waist/Chest |

In Tables 5 and 6, estimated data concerning exposure doses provided to plurality of tumour locations by LED matrices of different LED packing density (1.875 LED/cm² and 10 LED/cm², respectively). The modern LED means provide an option of short pulse mode of the photodynamic therapy.

TABLE 5

| 1.875 LEDs/cm2 3.75 W/cm2 | | | LED power | Future LEDs potential Kilojoules delivered in | | | |
|---|---|---|---|---|---|---|---|
| cm (X) | cm (Y) | cm2 | Kilowatts | eff. @ 50% | 60 s | 3600 s (1 hr) | Applications |
| 10 | 16 | 160 | 0.60 | 0.300 | 0.018 | 1.1 | Panel |
| 35 | 10 | 350 | 1.31 | 0.656 | 0.039 | 2.4 | 14" × 4" Arm |
| 50 | 10 | 500 | 1.88 | 0.938 | 0.056 | 3.4 | 20" × 4" Thigh |
| 90 | 10 | 900 | 3.38 | 1.688 | 0.101 | 6.1 | 36" × 4" Waist |
| 90 | 15 | 1350 | 5.06 | 2.531 | 0.152 | 9.1 | 36" × 6" Waist |
| 110 | 15 | 1650 | 6.19 | 3.094 | 0.186 | 11.1 | 43" × 6" Waist/Chest |
| 130 | 15 | 1950 | 7.31 | 3.656 | 0.219 | 13.2 | 51" × 6" Waist/Chest |

TABLE 6

| 10 LEDs/cm2 20 W/cm2 | | | LED power | Future LEDs potential Kilojoules delivered in | | | |
|---|---|---|---|---|---|---|---|
| cm (X) | cm (Y) | cm2 | Kilowatts | eff. @ 50% | 60 s | 3600 s (1 hr) | Applications |
| 10 | 16 | 160 | 3.20 | 1.600 | 0.096 | 5.8 | Panel |
| 35 | 10 | 350 | 7.00 | 3.500 | 0.210 | 12.6 | 14" × 4" Arm |
| 50 | 10 | 500 | 10.00 | 5.000 | 0.300 | 18.0 | 20" × 4" Thigh |
| 90 | 10 | 900 | 18.00 | 9.000 | 0.540 | 32.4 | 36" × 4" Waist |
| 90 | 15 | 1350 | 27.00 | 13.500 | 0.810 | 48.6 | 36" × 6" Waist |
| 110 | 15 | 1650 | 33.00 | 16.500 | 0.990 | 59.4 | 43" × 6" Waist/Chest |
| 130 | 15 | 1950 | 39.00 | 19.500 | 1.170 | 70.2 | 51" × 6" Waist/Chest |

Figure 10A:
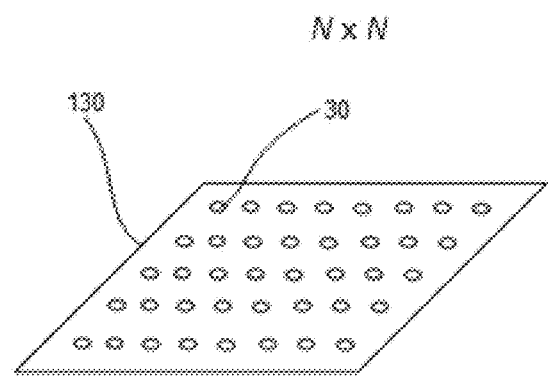
FIGS. 10a, 10b, 11a, 11b, 12a, and 12b schematically show propagation of light irradiated by LED matrices of different dimensions.

Reference is now made to FIGS. 10 (a and b), 11 (a and b) and 12 (a and b), presenting schematically operative principle of the present invention and. FIG. 10 shows a matrix of N×N LEDs 30, while FIGS. 11 and 12 correspond to LED matrices of M×M and K×K, respectively, thereat N<M<K.

It should be appreciated that there is a limitation of density of light intensity administered to the patient's body. The intensive narrow laser beam causes a burn. Consequently, a penetration depth of light used for photodynamic treatment is also limited according to Beer's law.

Figure 10B:
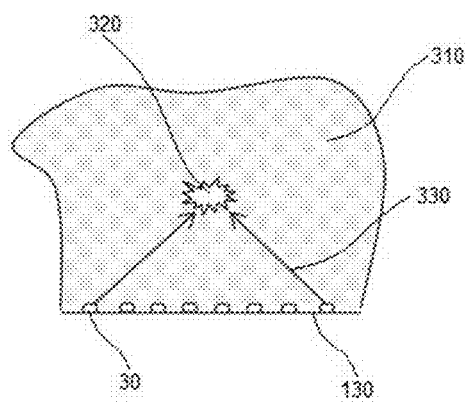
Figure 11A:
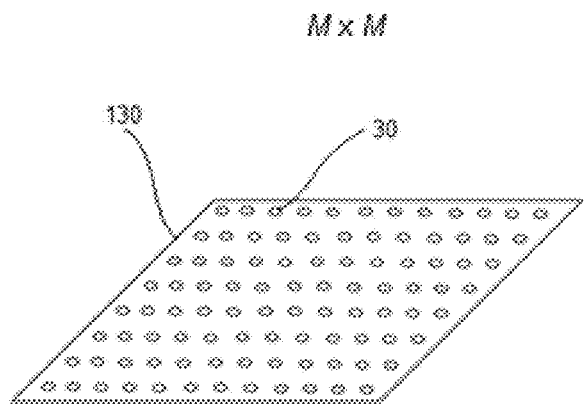
Figure 11B:
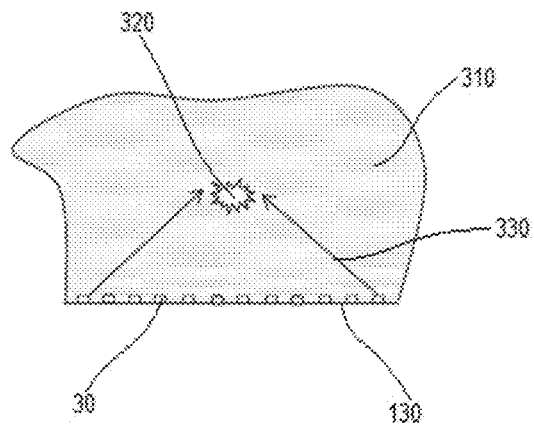
Figure 12A:
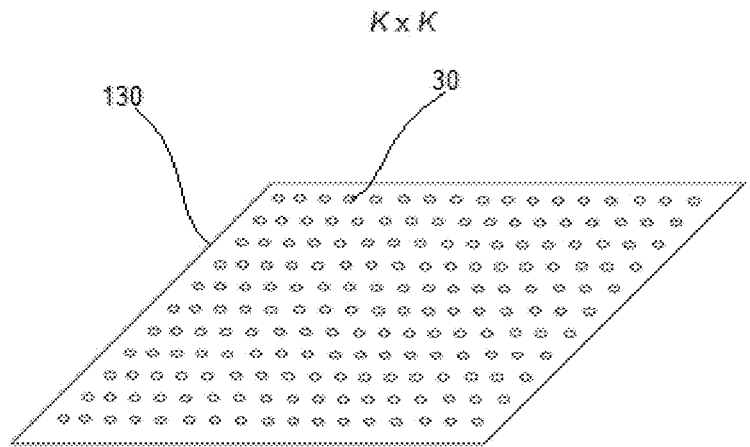
Figure 12B:
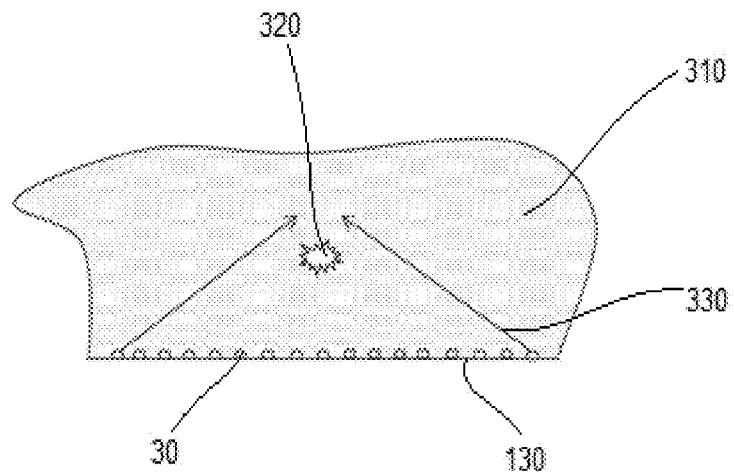

According to the present invention, an illuminated area of the patient's body 310 is two-dimensional. A growing number of side LEDs on a perimeter of the LED matrix also contribute into the resultant intensity in the target volume of a tumour 320. Light rays 330 originated from side LEDS reach the tumour 320. As seen in FIGS. 10b, 11b and 12b, the penetration depth grows with the matrix dimension. The described presentation is experimentally proved (see FIGS. 8 and 9). Specifically, in the model experiments on chicken breast, increase in the penetration depth from 4 cm up to 8 cm has been achieved.

An intermittent operation mode of the device is in the scope of the current invention. Intermitting active and inactive phases of illumination increases the performance of the drug because allows for cooling the skin during inactive phases to reduce heating effect of continuous light.

Some embodiments of the invention utilise a coolant loop that is in series with each segment of LEDs. The series configuration reduces water flow with increased resistance and the last segments will be the hottest depending on flow rate. The aforementioned is taken into consideration during the planning of the treatment schedule.

A parallel coolant loop is also contemplated in some embodiments of the invention where greater flow rates and possibly more consistently lower temperatures are required. The parallel configuration is defined by an arrangement of the invention whereby fluid enters all segments at the same time and leaves from all segments into a larger return tube.

In some embodiments of the invention ultimate control on the light output of the LEDs on each segment is provided: the output power to the unit may be altered in 0.1% steps from 0-100%

It is another objective of the invention to disclose treatment protocols for slowly raising the power level over the treatment area.

This might be important since as one penetrates a deep area, the closest flesh to the LED segment might receive a too powerful dosage and reduce drug effectiveness. On the other hand, a continuous low output may not achieve the depth of treatment. An optimal treatment protocol may be to gradually increase the light output over treatment time, allowing each measure of depth to receive the right amount of light until that depth is treated. Light is increased for deeper penetration in staged light increases.

In accordance with the current invention, a method of photodynamic therapy for treating cancer is disclosed. The aforesaid method comprises the steps of (a) providing a photodynamic therapeutic device for treating cancer; said device comprises a plurality of light emitting diodes positionable in proximity of a patient's body adapted to provide a light fluence to a lesion area and cooling means; (b) administering an effective dose of a photosensitizer in a lesion area of said patient's body; (c) positioning the device in proximity of said device to said patient's body; (d) irradiating said patient's body.

It is a core feature of the invention to provide the step of irradiating said lesion area which is characterized by power density ranging between 1 mW/cm$^2$ and 10,000 mW/cm$^2$ and treatment duration ranging between 100 sec and 3600 sec such that density of total energy incident to said lesion area is in a range between 0.01 J/cm$^2$ and 100 J/cm$^2$, thereat said step of irradiating said patient's body is performed by said photodynamic therapeutic device having a luminous surface of an area which is greater than 10 cm$^2$.

In accordance with a further embodiment of the current invention, the device positioned in proximity of said patient's body in a location is selected from the group consisting of a breast, an arm, a leg, a neck, an abdomen and any combination thereof.

In accordance with a further embodiment of the current invention, a mode of device operation is selected from the group consisting of a continuous mode, a pulse mode, an intermittent mode and any combination thereof.

In accordance with a further embodiment of the current invention, the step of positioning the device in proximity of said patient's body further comprises a step of preliminary positioning a silicon spacer therebetween.

In accordance with a further embodiment of the current invention, the step of irradiating at maximum light intensity at at least one wavelength is selected from the group consisting of: a wavelength of about 630 nm performed in coordination with said preceding step of administering an effective dose of a photosensitizer 5-aminolaevulinic acid (5-ALA); a wavelength of about 585 to about 740 nm performed in coordination with said preceding step of administering an effective dose of a photosensitizer 5,10,15,20-tetrakis(m-hydroxyphenyl) chlorin (Foscan); a wavelength of about 570 to about 670 nm is performed in coordination with said preceding step of administering an effective dose of a photosensitizer methyl aminolevulinate (Metvix); a wavelength of about 615 to about 800 nm performed in coordination with said preceding step of administering an effective dose of a photosensitizer Pd-bacteriopheophorbide (Tookad); a wavelength of about 600 to about 750 nm performed in coordination with said preceding step of administering an effective dose of a photosensitizer concentrated distillate of hematoporphyrins (Photofrin); a wavelength of about 450 to about 600 nm performed in coordination with said preceding step of administering an effective dose of a photosensitizer verteporfin (Visudyne) and any combination thereof.

In accordance with a further embodiment of the current invention, the step of irradiating is performed by said plurality of emitting diodes distributed along an inner surface of an annular structure.

In accordance with a further embodiment of the current invention, the step of irradiating is performed by LEDs grouped in a plurality of cooled units comprising at least two diodes; said cooled units are distributed along said inner surface of said annular structure.

In accordance with a further embodiment of the current invention, the step of positioning said device in proximity of said patient's breast further comprises a step of adjusting a length of said annular structure according to a patient's breast size.

In accordance with a further embodiment of the current invention, the step of positioning said device in proximity of said patient's breast further comprises steps of disposing said patient on a bearing surface in a prone position and putting in said patient's breast in said annular structure so that said annular structure embraces thereof and/or positioning the device in proximity of said patient's breast is performed frontally.

In accordance with a further embodiment of the current invention, the light intensity gradually increases over treatment time, allowing each measure of depth to receive an effective amount of light until that depth is treated.

In accordance with a further embodiment of the current invention, a device for photodynamic therapy for treating cancer is disclosed. The aforesaid device comprises a plurality of light emitting diodes postionable in proximity of a patient's body adapted to provide a light fluence to a lesion area and cooling means.

It is a core feature of the invention to provide the device having a luminous surface positioned in proximity of the patient's body part to be treated and having an area which is greater than 10 cm$^2$.

In accordance with a further embodiment of the current invention, the device is configured for irradiating said lesion area is characterized by power density ranging between 1 mW/cm$^2$ and 10,000 mW/cm$^2$ and treatment duration ranging between 150 sec and 3600 sec such that density of total energy incident to said lesion area is in a range between 0.01 J/cm$^2$ and 100 J/cm$^2$.

What is claimed is:

1. A method of photodynamic therapy for treating cancer; said method comprising the steps of:
   a. providing a photodynamic therapeutic device for treating cancer; said device comprises a copper circuit board, a plurality of light emitting diodes on said copper circuit board and positionable in proximity of a patient's body adapted to provide a light fluence to a lesion area and a passage connected to said copper circuit board to withdraw heat and accommodating a coolant circulating within said passage and removing heat generated by said plurality of light emitting diodes;
   wherein said passage is connected in fluid communication to a feeding pipe;
   b. administering an effective dose of a photosensitizer in a lesion area of said patient's body;
   c. positioning the device in proximity of said lesion area;
   d. irradiating said lesion area;
   e. transferring heat generated by said plurality of light emitting diodes through said copper circuit board to said passage;
   f. removing said generated heat from said passage by said coolant circulating within said passage;
   wherein said step of irradiating said lesion area is characterized by power density ranging between 1 mW/cm$^2$ and 10,000 mW/cm$^2$ and treatment duration ranging between 150 sec and 3600 sec such that density of total energy incident to said lesion area is in a range between 0.01 J/cm$^2$ and 100 J/cm$^2$, thereat said step of irradiating said lesion area is performed by said photodynamic therapeutic device having a luminous surface of a total area which is greater than 10 cm$^2$.

2. The method according to claim 1, wherein said device is positioned in proximity of said patient's body in a location selected from the group consisting of a breast, an arm, a leg, a neck, an abdomen and any combination thereof.

3. The method according to claim 1, wherein a mode of device operation is selected from the group consisting of a continuous mode, a pulse mode, an intermittent mode and any combination thereof.

4. The method according to claim 1, wherein said step of positioning the device in proximity of said patient's body further comprises a step of preliminary positioning a silicon spacer between the device and said patient's body.

5. The method according to claim 1, wherein said step of irradiating at maximum light intensity at least one wavelength selected from the group consisting of: a wavelength of about 630 nm performed in coordination with said preceding step of administering an effective dose of a photosensitizer 5-aminolaevulinic acid (5-ALA); a wavelength of about 585 to about 740 nm performed in coordination with said preceding step of administering an effective dose of a photosensitizer 5,10,15,20-tetrakis(m-hydroxyphenyl) chlorin (Foscan); a wavelength of about 570 to about 670 nm is performed in coordination with said preceding step of administering an effective dose of a photosensitizer methyl aminolevulinate (Metvix); a wavelength of about 615 to about 800 nm performed in coordination with said preceding step of administering an effective dose of a photosensitizer Pd-bacteriopheophorbide (Tookad); a wavelength of about 600 to about 750 nm performed in coordination with said preceding step of administering an effective dose of a photosensitizer concentrated distillate of hematoporphyrins (Photofrin); a wavelength of about 450 to about 600 nm performed in coordination with said preceding step of administering an effective dose of a photosensitizer verteporfin (Visudyne) and any combination thereof.

6. The device according to claim 1, wherein said step of irradiating is performed by said plurality of emitting diodes distributed along an inner surface of an annular structure.

7. The method according to claim 6, wherein said step of irradiating is performed by LEDs grouped in a plurality of cooled units comprising at least two diodes; said cooled units are distributed along said inner surface of said annular structure.

8. The method according to claim 1, wherein said step of positioning said device in proximity of said patient's breast further comprises a step of adjusting a length of said annular structure according to a patient's breast size.

9. The method according to claim 1, wherein said step of positioning said device in proximity of said patient's breast further comprises steps of disposing said patient on a bearing surface in a prone position and putting in said patient's breast in said annular structure so that said annular structure embraces thereof and/or positioning the device in proximity of said patient's breast is performed frontally.

10. The method according to claim 1, wherein at said step of irradiating, light intensity gradually increases over treatment time, allowing each measure of depth to receive an effective amount of light until that depth is treated.

11. The method according to claim 1, wherein said copper circuit board is 0.005" thick.

12. The method according to claim 1, wherein said photodynamic therapeutic device comprises a plurality of segments.

13. The method according to claim 12, wherein each segment contains 2 to 40 high power LEDs and would require up to 100 watts of heat removal for each segment.

14. The method according to claim 12, wherein each segment contains one of said copper circuit boards.

15. The method according to claim 12, wherein said segments have a clear silicone spacer mat directly in front of the LEDs to protect and to remove the possibility of a lens of the LED directly coming into contact with the skin and causing direct heat transfer.

16. The method according to claim 15, wherein said clear silicone spacer mat is 0.3-0.5 cm thick.

17. The method according to claim 15, wherein the LEDs are soldered directly to the copper circuit board.

18. The method according to claim 1, wherein said coolant is not in direct contact with said light emitting diodes.

* * * * *